US009681955B2

(12) United States Patent
Jordan et al.

(10) Patent No.: US 9,681,955 B2
(45) Date of Patent: *Jun. 20, 2017

(54) APPLICATION OF DIFFUSION HARDENED MATERIAL

(71) Applicant: Smith & Nephew, Inc., Memphis, TN (US)

(72) Inventors: Jason Sean Jordan, Hernando, MS (US); Vivek Devidas Pawar, Germantown, TN (US); Mark Ellsworth Nadzadi, Alameda, TN (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/937,199

(22) Filed: Nov. 10, 2015

(65) Prior Publication Data
US 2016/0095707 A1    Apr. 7, 2016

Related U.S. Application Data

(63) Continuation of application No. 13/697,773, filed as application No. PCT/US2011/037011 on May 18, 2011, now Pat. No. 9,180,012.
(Continued)

(51) Int. Cl.
*A61F 2/32* (2006.01)
*A61F 2/30* (2006.01)
(Continued)

(52) U.S. Cl.
CPC ............ *A61F 2/30767* (2013.01); *A61F 2/32* (2013.01); *A61F 2/38* (2013.01); *A61F 2/389* (2013.01);
(Continued)

(58) Field of Classification Search
CPC .. A61F 2/38; A61F 2/3859; A61F 2220/0025; A61F 2/30; A61F 2/32; A61F 2/30767
See application file for complete search history.

(56) References Cited

U.S. PATENT DOCUMENTS

| 4,340,978 A | 7/1982 | Buechel et al. |
| 6,726,725 B2 | 4/2004 | Hunter et al. |

(Continued)

FOREIGN PATENT DOCUMENTS

WO    2008154593 A1    12/2008

OTHER PUBLICATIONS

Springer, "McKeever Hemiarthroplasty of the Knee in Patients Less Than Sixty Years Old", J Bone Joint Surg Am. 2006;88:366-371.
(Continued)

*Primary Examiner* — Jason-Dennis Stewart
(74) *Attorney, Agent, or Firm* — Taft Stettinius & Hollister LLP

(57) ABSTRACT

An implant having components comprising an oxidized zirconium bearing surface adapted to decrease pain, lower friction, and minimize wear when coupled with natural femoral articular cartilage. The implant components also provide for reduced backside wear effects in fixed and mobile implants. The implant components further provide for more ideal wear coupling between components in mobile bearing implants.

19 Claims, 11 Drawing Sheets

Related U.S. Application Data

(60) Provisional application No. 61/345,801, filed on May 18, 2010, provisional application No. 61/389,349, filed on Oct. 4, 2010, provisional application No. 61/442,562, filed on Feb. 14, 2011.

(51) Int. Cl.

| | | |
|---|---|---|
| *A61F 2/42* | (2006.01) | |
| *A61F 2/44* | (2006.01) | |
| *A61L 27/30* | (2006.01) | |
| *A61L 27/50* | (2006.01) | |
| *A61F 2/38* | (2006.01) | |
| *A61L 27/10* | (2006.01) | |
| *A61L 27/04* | (2006.01) | |

(52) U.S. Cl.
CPC .......... *A61F 2/4202* (2013.01); *A61F 2/4425* (2013.01); *A61L 27/04* (2013.01); *A61L 27/10* (2013.01); *A61L 27/306* (2013.01); *A61L 27/50* (2013.01); *A61F 2002/30922* (2013.01); *A61F 2002/3208* (2013.01); *A61F 2310/00592* (2013.01); *A61L 2430/24* (2013.01)

(56) References Cited

U.S. PATENT DOCUMENTS

| | | | |
|---|---|---|---|
| 7,025,790 | B2 | 4/2006 | Parks et al. |
| 2004/0002766 | A1* | 1/2004 | Hunter ............... A61F 2/30767 623/20.21 |
| 2004/0034432 | A1 | 2/2004 | Hughes et al. |
| 2007/0137734 | A1 | 6/2007 | Pawar et al. |
| 2007/0173952 | A1 | 7/2007 | Hermansson et al. |
| 2008/0289729 | A1 | 11/2008 | Pawar et al. |
| 2009/0265013 | A1 | 10/2009 | Mandell |

OTHER PUBLICATIONS

International Search Report and Written Opinion issued for PCT/US2011/037011, dated Jan. 10, 2012, 10 pages.

European Examination Report; European Patent Office; European Patent Application No. 11784177.5; Dec. 7, 2015; 7 pages.

European Examination Report; European Patent Office; European Patent Application No. 11784177.5; Mar. 29, 2017; 4 pages.

\* cited by examiner

FIG. 5A
| PARTS | OXIDE OUTSIDE WORN AREA | OXIDE INSIDE WORN AREA BUT NOT WORN THROUGH THE OXIDE | WEAR OF OXIDE | DHZ AWAY FROM THE WEAR TRACK | DHZ IN AREA WHERE OXIDE WAS WORN THROUGH AND DHZ WAS THE BEARING PORTION | WEAR OF DHZ |
|---|---|---|---|---|---|---|
| FEMORAL | 5.6 | 4.8 | 0.8 | 18.0 | --- | --- |
| TIBIA BASE | 5.5 | 5.0 | 0.5 | 19.7 | --- | --- |
| INSERT-PROXIMAL | 4.8 | 3.1 | 1.7 | 18.1 | --- | --- |
| INSERT-DISTAL | 5.3 | 3.3 | 2.0 | 19.0 | 15.7 | 3.3 |
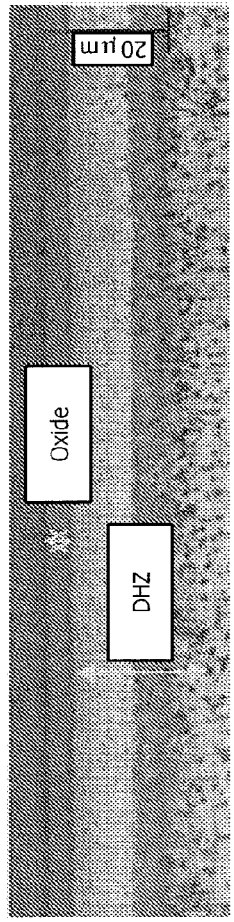
FIG. 5B
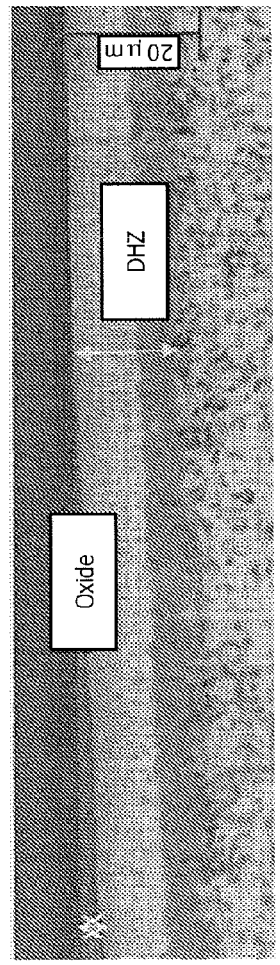
FIG. 5C

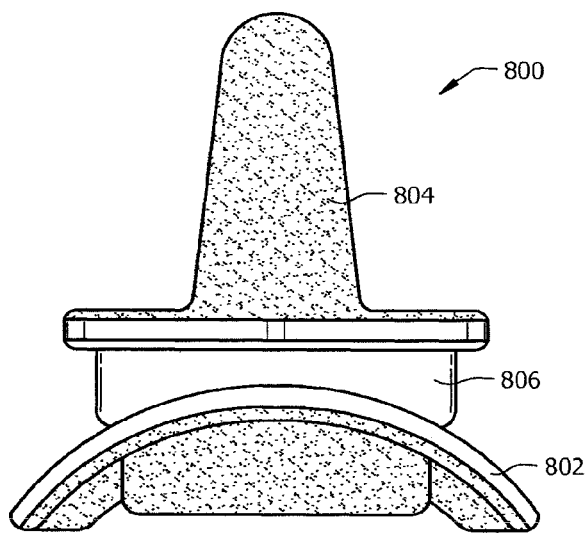
FIG. 8
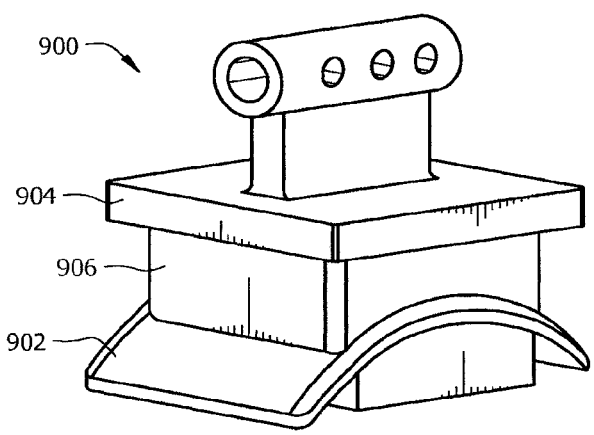
FIG. 9
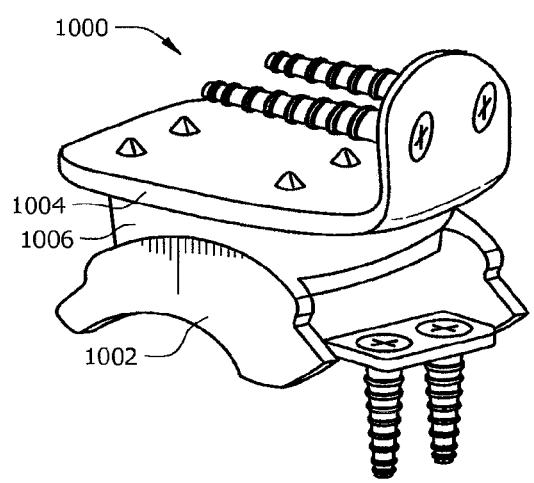
FIG. 10
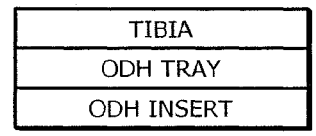
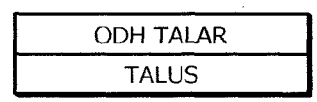
FIG. 11

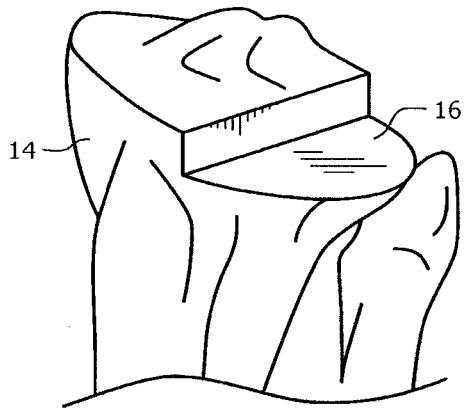
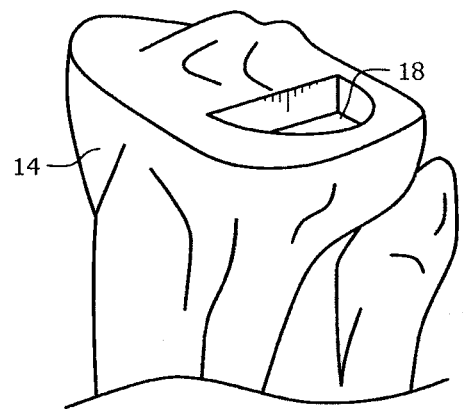
*FIG. 18*  *FIG. 19*
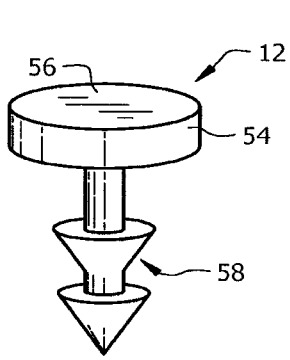
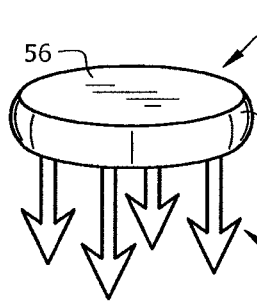
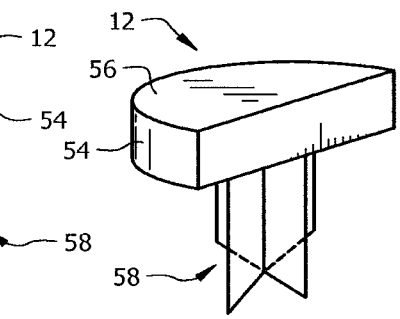
*FIG. 20A*  *FIG. 20B*  *FIG. 20C*
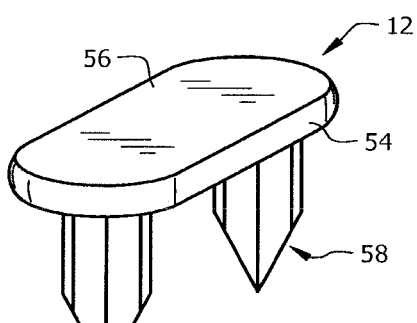
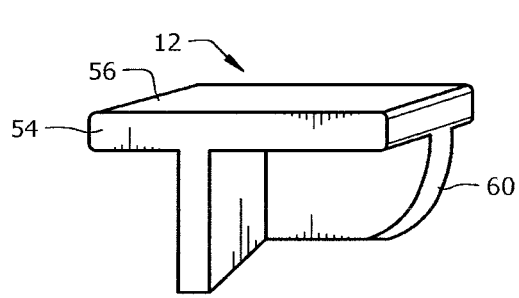
*FIG. 20D*  *FIG. 20E*

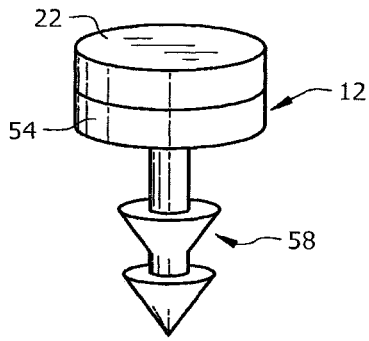
FIG. 20F
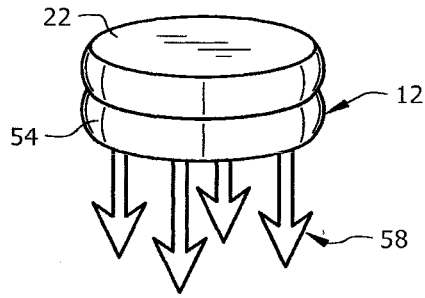
FIG. 20G
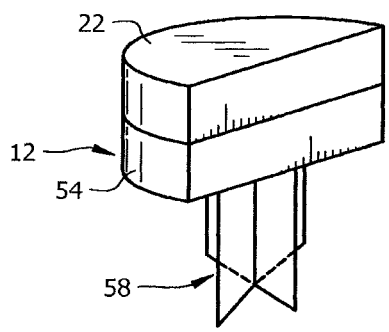
FIG. 20H
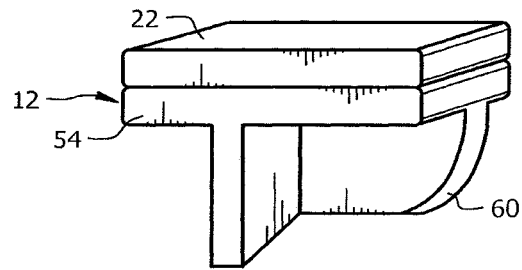
FIG. 20I
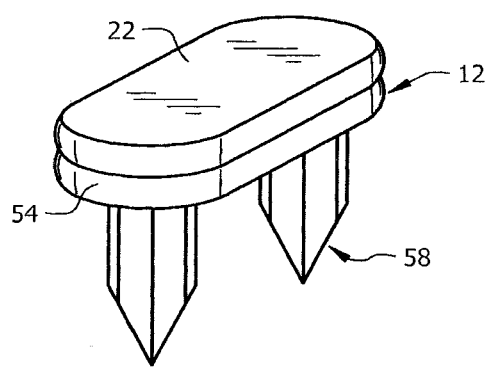
FIG. 20J
FIG. 21

APPLICATION OF DIFFUSION HARDENED MATERIAL

CROSS-REFERENCE TO RELATED APPLICATIONS

This application is a continuation of U.S. patent application Ser. No. 13/697,773 filed on May 22, 2013 and issuing as U.S. Pat. No. 9,180,012, which is a U.S. national stage filing of International Application No. PCT/US2011/037011 filed on May 18, 2011, which claims priority to U.S. Provisional Application No. 61/345,801 filed on May 18, 2010, U.S. Provisional Application No. 61/389,349 filed on Oct. 4, 2010, and U.S. Provisional Application No. 61/442,562 filed on Feb. 14, 2011, the disclosures of which are incorporated herein by reference in their entirety.

TECHNICAL FIELD

The present invention relates generally to orthopedic prosthetic devices, and more particularly to prosthetic devices employing diffusion-hardened surfaces.

BACKGROUND OF THE INVENTION

In fixed bearing tri-component implants, such as knee or ankle implants, the locking interface between the polyethylene bearing construct and the metal base construct can be a significant source of wear debris. More particularly, the sliding motions (or micromotion) in the junction between the polyethylene bearing construct and the metal base construct produce polyethylene particles that can migrate into the body. Small abrasive particles can also migrate into the interface between the polyethylene bearing construct and the metal base construct and scratch the metal base construct, particularly when the metal base construct is formed out of titanium. This issue of "backside wear" has generally been a long-term problem in tri-component implant devices such as total knee arthroplasty (TKA), total ankle arthroplasty (TAA), spinal implants, and bi-polar hip implants. For instance, the backside wear in TKA occurs at the interface between a surface of a tibial insert and a surface of a tibial tray and at the interface between a surface of an intermediate bearing component and a surface of a tibial component in TAA.

Particles caused by backside wear may cause osteolysis and other degenerative conditions. These particles may further act as an abrasive and accelerate wear over time. Efforts have been made to reduce backside wear effects by using more wear-resistant cross-linked polyethylene (XLPE) inserts, which are generally more brittle and stiffer than conventional polyethylene inserts. As such, XLPE inserts may be disadvantageous in high impact applications, such as knee and ankle replacement applications. Other attempts to address the backside wear issue also include polishing techniques such as polishing the titanium mating surface of the metal base construct, e.g., tibial trays or tibial components. While polishing techniques may reduce backside wear, these techniques may not significantly reduce the number of wear particles created. Other attempts to reduce backside wear have focused on refining and improving locking features (e.g., dovetail grooves) to better secure and restrain the tibial insert from moving relative to other fixed components, e.g., the tibial tray. The basis for those attempts included the theory that by preventing micromotion, backside wear could be minimized and wear particles would not occur. However, such efforts have made connecting the insert to the tray in a surgical procedure more difficult, because such locking features generally operate under very tight tolerances. Soft tissue, blood, and bone chips may interfere with the tight tolerances of such locking features and may make assembly very difficult and time consuming. If any wear particles or hard biological matter (e.g., bone chips) do end up between the tight fitting locking mechanism components, wear rate may be further accelerated. In short, backside wear remains a problem as the prior art has failed to completely eliminate micromotion. These attempts have left surgeons frustrated with tight-fitting inserts.

In mobile bearing implants, there are also other problems caused by the generally free movement of the inserts as compared to the fixed components in fixed bearing implants. Mobile bearing components may be used with uni-compartmental, bi-compartmental, or tri-compartmental prosthetic devices and are thought by some to provide a "natural" movement, "natural" feeling, and/or also serve as "self-adjusting" means to compensate for slight misalignment. However, in most cases, mobile bearing components comprise less than ideal wear couples. For example, a typical mobile bearing of the prior art may comprise a tibial tray made from polished titanium or stainless steel, and a tibial insert made of conventional or cross-linked polyethylene. When the tibial insert articulates against the tray, a wear couple is formed. Such mobile-bearing wear couples of the prior art are not ideal because titanium and/or stainless steel do not have superior bearing properties when used with polyethylene or articular cartilage. Similarly, the prior art mobile bearing ankle prostheses suffer from such non-ideal coupling of the components.

There are also disadvantages with McKeever and McIntosh-style tibial hemi-arthroplasty devices that have been provided in the prior art to address problems involving unicondylar knee replacements performed in patients having a femur which may not need replacing. In particular, these devices are made from conventional materials (e.g., titanium, stainless steel, Vitallium metal) which are less than ideal for articulation with both polyethylene and natural articular cartilage. See Springer et al., "McKeever Hemiarthroplasty of the Knee in Patients Less Than Sixty Years Old," J Bone Joint Surg Am. 2006, 88:366-371.

In view of the above, there exists a need for tri-component implants, whether fixed bearing or mobile bearing, with strengthened, low friction, highly wear resistant surfaces that significantly reduce backside wear, and provide more ideal coupling between the components and with improved bearing surface properties with natural articulating cartilage.

BRIEF SUMMARY OF THE INVENTION

The present disclosure provides a device having a highly compatible, superior, low-friction wear couple with the natural articulating cartilage of a patient.

The present disclosure provides an implant with reduced wear rate between implant components, and between an implant component and the natural articulating cartilage.

The present disclosure provides an implant with minimal backside wear effects caused by micromotion that does not rely on tight-fitting inserts.

The present disclosure provides an implant with more ideal wear coupling between components for mobile bearing implants.

Further, the present disclosure provides an implant with minimal backside wear without sacrificing an increase in brittleness for improved wear resistance.

According to one aspect of the present disclosure, there is provided a medical implant comprising: a first component having a first surface; a second component having a second surface and a third surface; and a third component having a fourth surface; wherein said first surface is configured to contact said second surface, said first and second surfaces are configured to be in generally opposing facing relation to one another;

wherein said third surface is configured to contact said fourth surface, said third and fourth surfaces are configured to be in generally opposing facing relation to one another; wherein a portion of each of said first, second, third, and fourth bearing surfaces comprises: a diffusion hardened zone that is in contact with a substrate; a substantially defect-free ceramic layer overlaying said diffusion hardened zone, wherein said ceramic layer has a thickness of about 0.1 to 25 microns and said diffusion hardened zone has a thickness of greater than 2 microns.

In one embodiment, said medical implant is selected from a group consisting of a tibial hemiarthroplasty component, a total knee replacement implant, an ankle replacement implant, a lumbar disc replacement implant, and a bi-polar hip implant. In another embodiment, said diffusion hardened zone has a thickness of greater than 5 microns. In another embodiment, at least one of said first, second, third, and fourth surfaces further comprises a metallic hardened layer in contact with the top of the ceramic layer. In another embodiment, the ceramic layer comprises a secondary phase, wherein the secondary phase is distinct through the entire thickness of the ceramic layer; and the diffusion hardened zone has a layered structure comprising at least two distinct layers under metallographic analysis.

In yet another embodiment, the surfaces of one generally opposing facing pair of said first, second, third, or fourth surfaces are attached to one another. In another embodiment, the surfaces of one generally opposing facing pair of said first, second, third, or fourth surfaces are configured to articulate against one another. In another embodiment, at least one of said first, second, third, and fourth surfaces consist of said diffusion hardened zone.

According to another aspect of the present disclosure, there is provided a medical implant comprising: a first portion having a first bearing surface with a first radius; a second portion having a second bearing surface with a second radius; wherein said first bearing surface is configured to couple with said second bearing surface, said coupling is defined by a maximum ratio between said first radius and said second radius of 1:1.05; wherein a portion of each bearing surface comprises: a diffusion hardened zone that is in contact with a substrate; a substantially defect-free ceramic layer overlaying said diffusion hardened zone, wherein said ceramic layer has a thickness of about 0.1 to 25 microns and said diffusion hardened zone has a thickness of greater than 2 microns.

In one embodiment, said medical implant is selected from a group consisting of a tibial hemiarthroplasty component, a total knee replacement implant, an ankle replacement implant, a lumbar disc replacement implant, and a bi-polar hip implant. In another embodiment, said diffusion hardened zone has a thickness of greater than 5 microns. In another embodiment, said at least one bearing surface further comprises a metallic hardened layer in contact with the top of the ceramic layer. In another embodiment, the ceramic layer comprises a secondary phase, wherein the secondary phase is distinct through the entire thickness of the ceramic layer; and the diffusion hardened zone has a layered structure comprising at least two distinct layers under metallographic analysis.

According to another aspect of the present disclosure, there is provided a medical implant comprising: a biocompatible metal or metal alloy substrate having at least one surface configured to articulate against cartilage around a distal portion of a femoral of a patient, wherein a portion of said surface configured for articulation comprises: a diffusion hardened zone that is in contact with a substrate; a substantially defect-free ceramic layer overlaying said diffusion hardened zone, wherein said ceramic layer has a thickness of about 0.1 to 25 microns and said diffusion hardened zone has a thickness of greater than 2 microns.

In one embodiment, the medical implant comprises a tibial hemiarthroplasty component. In another embodiment, said surface consists of said diffusion hardened zone.

According to yet another aspect of the present disclosure, there is provided a medical implant comprising: a femoral component having a first surface; a tibial component having a second surface; and an insert configured to be interposed between said femoral component and said tibial component, said insert having a third surface and a fourth surface; wherein said first surface is configured to be in generally opposing facing relation with said third surface and configured to articulate against said third surface; wherein said second surface is configured to be in generally opposing facing relation with said fourth surface; wherein a portion of each of said first, second, third, and fourth bearing surfaces comprises: a diffusion hardened zone that is in contact with a substrate; a substantially defect-free ceramic layer overlaying said diffusion hardened zone, wherein said ceramic layer has a thickness of about 0.1 to 25 microns and said diffusion hardened zone has a thickness of greater than 2 microns.

In one embodiment, said second surface is attached to said fourth surface. In another embodiment, said diffusion hardened zone has a thickness of greater than 5 microns. In another embodiment, said contacting surface further comprises a metallic hardened layer in contact with the top of the ceramic layer.

The foregoing has outlined rather broadly the features and technical advantages of the embodiments present disclosure in order that the detailed description of these embodiments that follows may be better understood. Additional features and advantages of the embodiments of the present disclosure will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 5A represents the thickness measurement of the oxide and diffusion hardened layer of the components of a knee implant according to one aspect of the present disclosure after a wear test.

FIGS. 5B-5C are metallographic images showing the different layers of certain portions of one component of a knee implant according to one aspect of the present disclosure after a wear test.

FIGS. 6-10 are perspective views of the various ankle implant embodiments of the present disclosure.

FIG. 11 is a representation of an exemplary arrangement of an ankle prosthesis in accordance with the present disclosure.

FIG. 18 is a perspective view of the tibia of the embodiment of the present disclosure shown in FIGS. 16-17.

FIG. 19 is a perspective view of the tibia of another embodiment of the present disclosure.

FIGS. 20A-20E are perspective views of various one-piece embodiments of the present disclosure.

FIGS. 20E-20J are perspective views of various multiple-piece embodiments of the present disclosure.

FIG. 21 is a representation of an exemplary arrangement of the embodiments of the present disclosure.

DETAILED DESCRIPTION OF THE INVENTION

Figure 1:
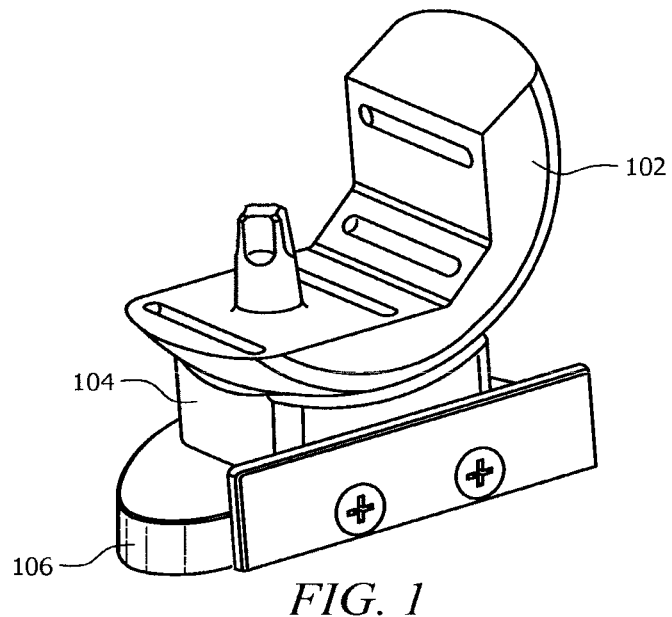
FIG. 1 is an illustration of a tri-component knee prosthesis according to one aspect of the present disclosure.

The present disclosure provides medical implants, particularly orthopedic implants, with articulating or bearing surfaces comprising a diffusion hardened composition with an oxide layer that is substantially defect-free and a diffusion hardened zone with a thickness that is greater than the prior art compositions, e.g., greater than 2 microns. In some embodiments, the diffusion hardened zone has a thickness of 5 to 70 microns. The diffusion hardened zone may have a thickness of 10 to 50 microns. The diffusion hardened zone may have a thickness of 15 to 30 microns. In particular, the diffusion hardened composition of the present disclosure is described in detail in U.S. Pat. No. 7,550,209 to Pawar et al. and co-pending U.S. application Ser. Nos. 12/127,413 and 12/244,492, the disclosures of which are incorporated by reference.

In one embodiment, the diffusion hardened composition of the present disclosure comprises a metallic substrate, such as a biocompatible alloy, having a ceramic surface. Examples of biocompatible alloys include alloys that are made from either zirconium or titanium or tantalum or niobium or hafnium or combination thereof, such as cobalt-chromium-molybdenum, titanium-aluminum-vanadium, nickel-titanium and zirconium-niobium. The ceramic surface may be formed by various processes known to those skilled in the art, such as air oxidation. Beneath the oxide layer is a hard, oxygen-rich diffusion layer called the diffusion hardened zone. According to one aspect of the present disclosure, the diffusion hardened zone may be defined as the region which has hardness at least 1.1 times of the substrate hardness.

The composition of the present disclosure may have a totality of the thickness of the ceramic (or oxide) layer and the diffusion hardened zone that is greater than 5 microns, and preferably greater than 10 microns. In some embodiments, the ceramic layer may or may not be present (it can range in thickness from 0 to 25 microns). Accordingly, the diffusion hardened zone of these embodiments may have a thickness of greater than 5 microns (and preferably greater than 10 microns) with no ceramic layer above it or an infinitesimally small ceramic layer above it. Where both layers are present, the ceramic layer is on the surface and is above the diffusion hardened zone. Examples of metal or metal alloy substrates, such as those mentioned above, and diffusion hardening species appropriate for the diffusion hardened composition of the present disclosure are described in U.S. Pat. No. 7,550,209 and co-pending U.S. application Ser. Nos. 12/127,413 and 12/244,492. For example, the diffusion hardening species may include oxygen, nitrogen, boron, carbon, and any combination thereof.

While the diffusion hardened zone is one of the two aforementioned layers, the diffusion hardened zone itself consists of at least two distinct layers (visible by metallographic analysis). The first layer of the diffusion hardened zone has a relatively high concentration of diffusion hardening species (higher than that of the bulk metal or metal alloy substrate, e.g., zirconium or zirconium alloy) and may be saturated with the diffusion hardening species. In embodiments involving zirconium as the substrate, the zirconium in the first layer is predominantly alpha phase zirconium (the first layer of the diffusion hardened zone is that layer which is closest to the ceramic layer, or, where the ceramic layer is absent, the first layer is that layer which is nearest to the surface of the composition). The second layer is below the first layer and has a lower content of diffusion hardening species than the first layer. The diffusion hardened zone has a diffusion hardening species concentration profile such that, in one or more cross-sections of the diffusion hardened zone, the concentration of diffusion hardening species decreases as either an error function, an exponential function, a near uniform distribution, or sequential combinations thereof.

The layered structure of the diffusion hardened zone can be detected by metallographic analytical techniques known to those of ordinary skill in the art. These include, but are not limited to, anodization, heat tinting, x-ray diffraction, Auger spectroscopy, depth profiling, etc.

The diffusion hardened composition of the present invention is particularly applicable to tri-component knee replacement implants, whether fixed or mobile bearings. Typically, tri-component knee implants include a tibial component or tray, an insert, and a femoral component. An example of the tri-component implant, e.g., hemiarthroplasty knee replacement prosthesis, is illustrated in FIG. 1. Specifically, FIG. 1 shows a femoral component 102, an intermediate insert 104, and a tibial component 106. The implant of FIG. 1 may be a fixed bearing or mobile implant. In a fixed bearing implant, the distal surface of the intermediate insert 104 would be attached to the proximal surface of the tibial component 106. The components may be attached to one another by attachment means known in the art. At least the attached surfaces of the tibial component 106 and the intermediate insert 104 are generally level or flat and correspond to one another. In a mobile implant, the intermediate insert 104 would not be attached to either the tibial component 106 or the femoral component 102, and the distal surface of the insert 104 is configured to articulate against the proximal surface of the tibial component 106. In both fixed bearing and mobile implants, the proximal surface of the insert 104 is configured to articulate against the distal surface of the femoral component 102. Other embodiments may include the total knee replacement implants instead of only hemiarthroplasty implant.

Typically, the tibial base component 106 and the femoral component 102 are formed from metal such as cobalt chrome, and the intermediate bearing insert 104 comprises a softer material such as polyethylene or cross-linked ultra-high molecular weight polyethylene (XLPE). While these materials suffer from the disadvantages discussed above, particularly debris formation by and accelerated wear of polyethylene, they are often used instead of ceramics because prior art ceramics are unlikely to withstand the combined compressive and anteroposterior (A/P) shear loading typically endured by a total knee replacement implant.

Figure 2:
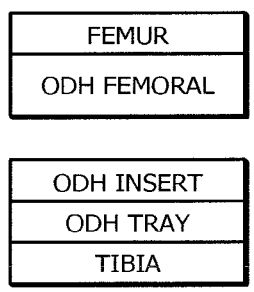
FIG. 2 is a representation of the one exemplary arrangement of a tri-component implant embodiment of the present disclosure.

Referring to FIG. 2, in the preferred embodiment, at least the articulating or load bearing surfaces of the components comprise the diffusion hardened composition of the present disclosure (referred to as "ODH" in FIG. 2). In particular, these articulating or load bearing surfaces include (1) the proximal surface of the tibial component that contacts the insert, (2) the distal surface of the insert, (3) the proximal surface of the insert that contacts the femoral component, and (4) the distal surface of the femoral component. As shown, the embodiment comprises two pairs of diffusion hardened surfaces, where the surfaces articulate against and/or exert a force upon one another. In the preferred embodiment, all the bearing surfaces comprise the diffusion hardened composition of the present disclosure. This combination is not possible in the prior art due to the lower wear and damage resistant characteristics of the prior art ceramics or substrates with a ceramic surface.

Figure 3:
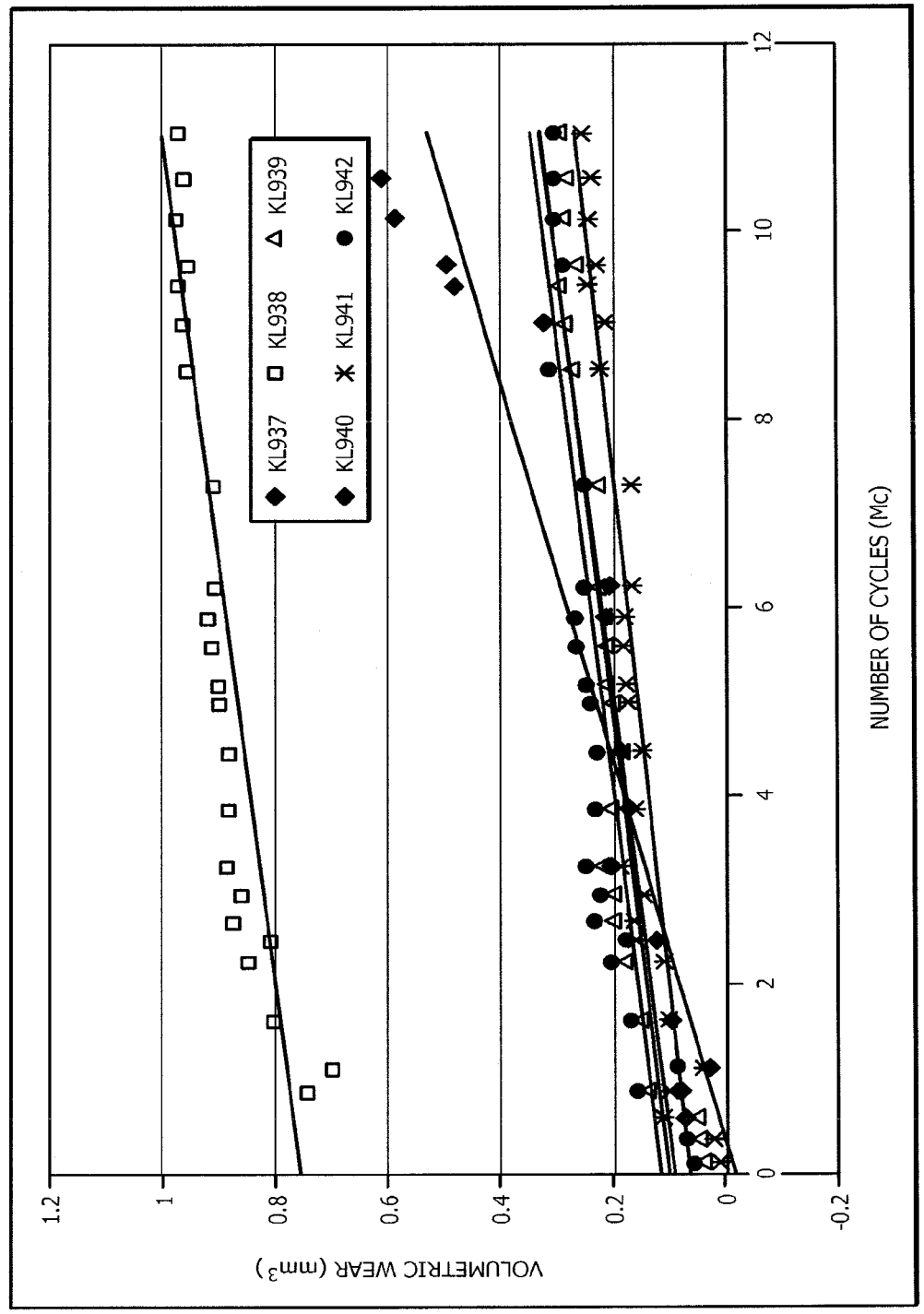
FIG. 3 is a chart summarizing the results from testing the wear of three sets of tri-component knee prosthesis according to one aspect of the present disclosure.

FIG. 3 is a chart summarizing the results from testing a wear of three sets of a tri-component knee implant, e.g., the femoral component, the insert, and the tibial component, where the articulating or load bearing surfaces of the implants comprise the diffusion hardened composition of the present disclosure. The test simulated wear that takes place during use of three sets of mobile knee implants, where the femoral and tibial base are affixed in place and the insert is unfastened and interposed between those components. The testing arrangement replicates a mobile knee implant. The testing equipment simulated the various movements of a patient, such as walking, bending, jumping, over about 11 Mc wear cycles where one Mc is one million cycles. The aberration in the result of component KL938 was due to a malfunction in the machine that tested the wear on component KL938.

Figure 4:
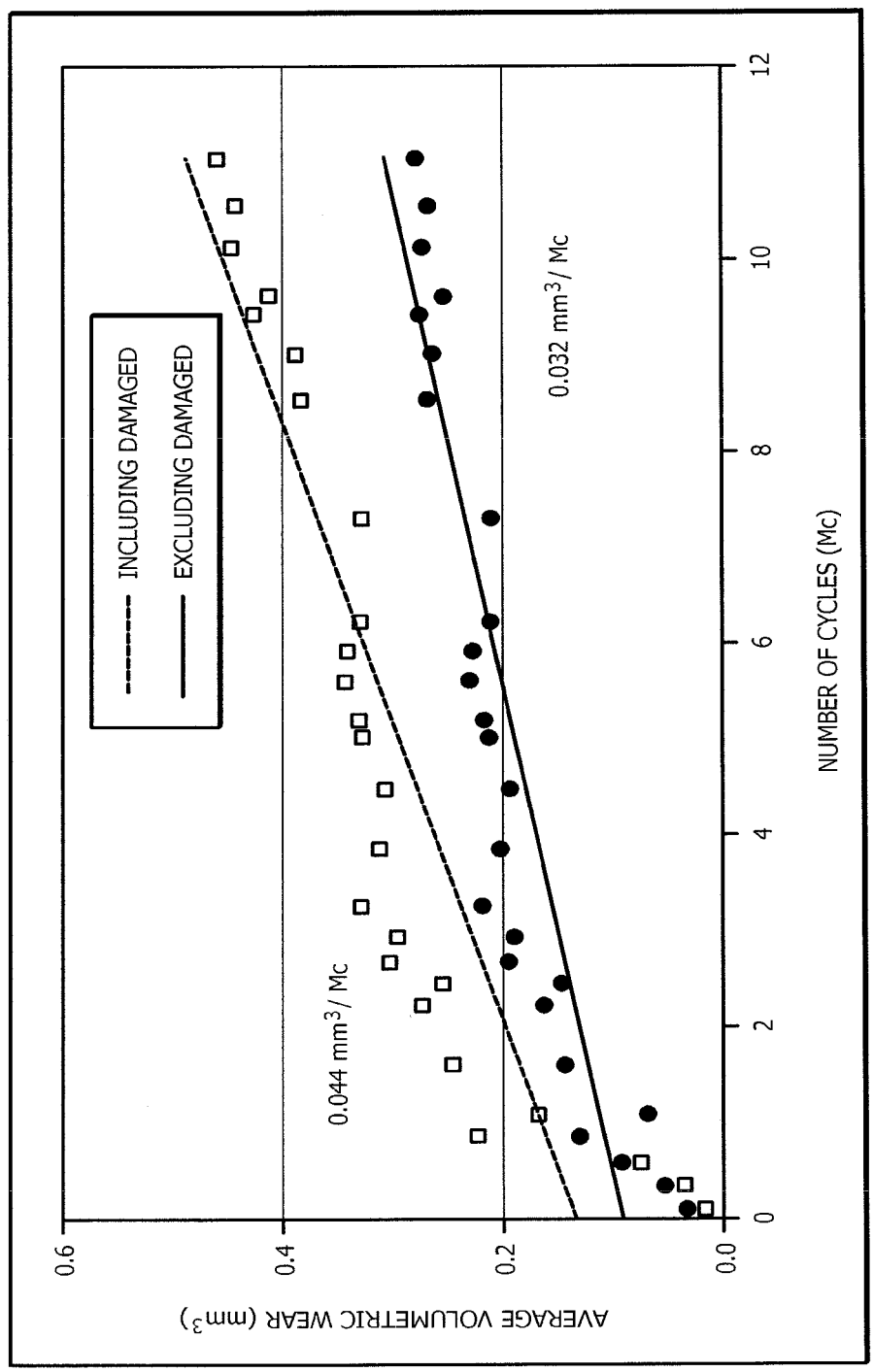
FIG. 4 represents the average volumetric wear of the three sets of components from FIG. 20.
Figure 6:
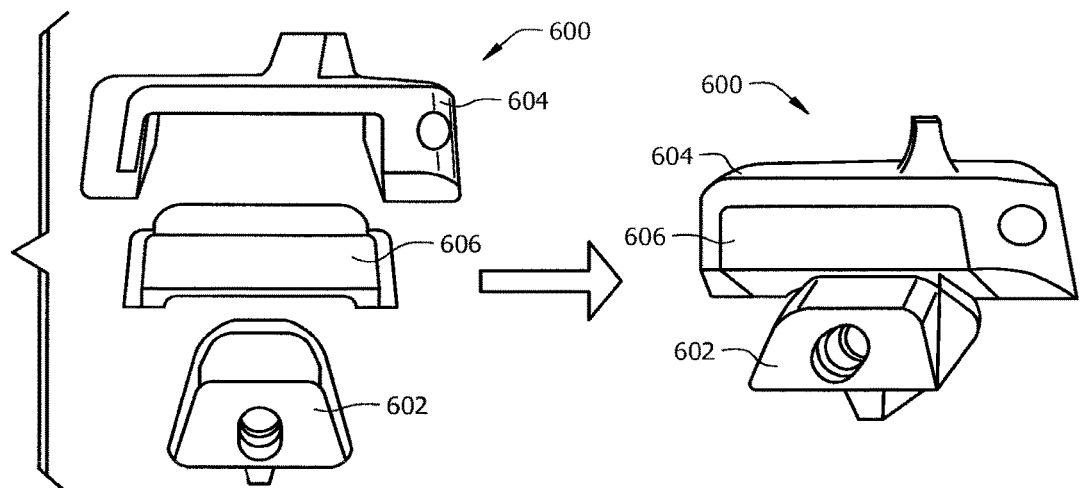
Figure 7:
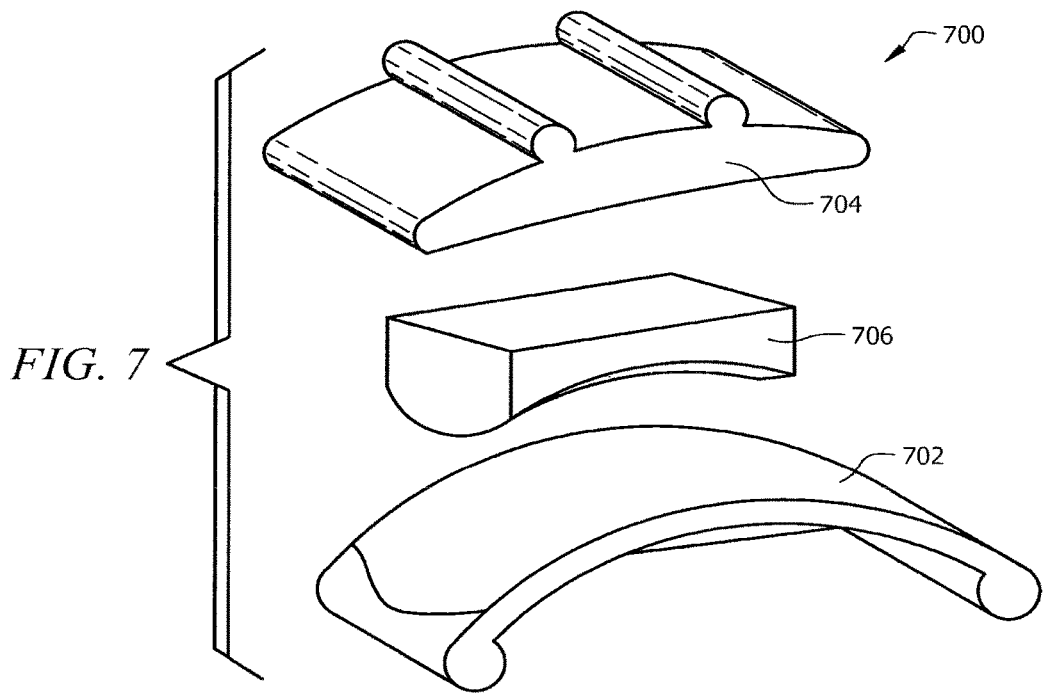

FIG. 3 shows that the wear of the components after ten million cycles was mostly around 0.3 mm$^3$. This is further confirmed in FIG. 4, which represents the average volumetric wear of the three sets of components from FIG. 3. FIG. 4 provides two sets of results: the first one includes the measurements of the defective component KL938 and the second one excludes the defective values. The results shown by FIGS. 3 and 4 demonstrate that the components of a tri-component implant having articulating or load bearing surfaces that comprise the diffusion hardened composition of the present disclosure exhibit a significantly higher wear resistance as compared to traditional bearing materials. Traditional bearing combinations include cobalt chrome on polyethylene and cobalt chrome on XLPE.

Table 1 below illustrates the improved wear rates of the diffusion hardened material of the present disclosure against polyethylene, XLPE, and itself, as compared to the traditional bearing materials of cobalt chrome.

TABLE 1

| Material | Wear Rate mm$^3$/Mc |
| --- | --- |
| Cobalt Chrome against Polyethylene | 20 to 25 |
| Cobalt Chrome against XLPE | 5 to 6 |
| Diffusion hardened composition of the present disclosure (ODH) against | 10 to 12 |
| ODH against XLPE | 0.6 |
| ODH against ODH | 0.1 |
| ODH against ODH against ODH (3 components) | 0.03-0.04 |

As shown in Table 1, the diffusion hardened material of the present disclosure ("ODH") is about twice as resistant to wear as cobalt chrome, a conventional material used in various implants including TKA, TAA, and spinal applications, when applied against polyethylene. The ODH material of the present disclosure is about 10 times as resistant to wear as cobalt chrome against XLPE. While the wear resistance is further improved by using the diffusion hardened composition of the present disclosure against itself, the most wear resistance is achieved when the diffusion hardened composition of the present invention on all three components. The use of ceramics on the articulating or bearing surfaces of all three components of a tri-component implant was not possible before due to the lower wear and damage resistant characteristics of the prior art materials.

FIG. 5A represents the measurement of the wear of the oxidation layer and the diffusion hardened zone (referred to as "DHZ" in FIG. 5A) of one tested set of tri-component knee implant, measured after the wear test. The unit measurement of the wear is in microns.

The column labeled as "Oxide outside worn area" shows the thickness of the oxide layer of the various components. For the femoral portion, the oxide layer thickness was about 5.6 microns. For the tibial base, the oxide layer thickness was about 5.5 microns. For the proximal side of the insert, the oxide layer thickness was about 4.8 microns. And for the distal side of the insert, the oxide layer thickness was about 5.3 microns. These values are contrasted with the thickness values measured at portions where the oxide layer is worn by the wear test, which are listed in the column labeled "Oxide inside worn area but not worn through the oxide." For the femoral portion, the worn oxide layer thickness was about 4.8 microns. For the tibial base, the worn oxide layer thickness was about 5.0 microns. For the proximal side of the insert, the worn oxide layer thickness was about 3.1 microns. And for the distal side of the insert, the worn oxide layer thickness was about 3.3 microns.

The column labeled as "DHZ away from the wear track" shows the thickness of the diffusion hardened zone of the various components. For the femoral portion, the DHZ thickness was about 18 microns. For the tibial base, the DHZ thickness was about 19.7 microns. For the proximal side of the insert, the DHZ thickness was about 18.1 microns. And for the distal side of the insert, the DHZ thickness was about 19 microns.

The column labeled "DHZ in area where oxide was worn through and DHZ was the bear portion" shows the remaining thickness of the diffusion hardened zone ("DHZ"). For the femoral component, tibial component, and proximal side of the insert, the oxide was not worn through; hence no corresponding values under the column "Wear of DHZ." For the distal side of the insert, the oxide did wear through and 15.7 microns of DHZ still remained to serve as the bearing portion after 11 Mc. There was a corresponding DHZ wear amount of 3.3 microns.

As reflected in FIG. 5A, after considerable use of the implants as demonstrated by the wear test, there was still a significant portion of diffusion hardened composition left for articulation. That is, even if the oxidation layer has been worn through, the more damage resistant and thicker diffusion hardened zone of the diffusion hardened composition of the present disclosure remains substantially intact to maintain proper articulation between the components.

FIGS. 5B-5C shows the cross section of different portions of the distal side of the insert of one of the three tested sets of the tri-component knee implants after the wear test. FIGS. 5B-5C show the oxide layer serving as the surface of the components of the implant and is on top of the diffusion hardened zone. In particular, FIG. 5B shows one cross section where the oxide has not worn through. FIG. 5C shows the cross section where the oxide has worn through and the diffusion hardened zone serves as the bearing surface. In FIG. 5B, the oxide layer is about 5 microns thick and diffusion hardened zone (DHZ) is about 18-19 microns thick. In FIG. 5C, the remaining diffusion hardened zone has a thickness of about 15 microns. It is apparent that the oxide is thinner in that region and is completely worn in some areas. While the oxide layer is worn, the DHZ continues to serve as a good bearing material. With previous oxidized surfaces, the exposed substrate would have been much softer than the diffusion hardened zone of the present disclosure. The softer prior art oxidized substrate, when exposed after the oxide layer is worn, would not have been a good bearing surface, thereby leading to even further accelerated wear. The appearance of the exposed region of the implants of FIGS. 5B-5C was macroscopically apparent (bright metallic). In one embodiment, the diffusion hardened composition of the present disclosure is characterized by a zirconium oxide on the surface and underneath a diffusion hardened zone that is greater than 2 microns thick. The oxide and the diffusion hardened zone of the present disclosure together offer better wear and damage resistant surfaces.

As shown, one embodiment includes components having an oxide layer thickness of about 5-6 microns and a DHZ thickness of about 18-20 microns. In other embodiments, however, one or more components of a tri-component implant do not include an oxide layer, or alternatively, an oxide layer that is at least 0.1 microns thick and at most 25 microns. Preferably, the oxide layer has a thickness of about 4 microns to 10 microns. In an embodiment with an oxide layer, the component may further include a metallic hardened layer in contact with the top of the oxide layer. In embodiments without the oxide layer, the oxide layer may be removed by means known to one skilled in the art, such as those described in U.S. Pat. No. 7,550,209 and co-pending U.S. application Ser. Nos. 12/127,413 and 12/244,492. One example to dissolve the oxide layer in the substrate. In another embodiment, the DHZ of one or more components of a tri-component implant has a thickness of at least 10 microns and at most 50 microns. Preferably, the DHZ has a thickness of about 15 microns to 25 microns.

FIGS. 5B and 5C are metallographic images showing the layered structure of the diffusion hardened zone in some embodiments. In one embodiment, the oxide is predominantly composed of stable monoclinic phase (>93% by volume). In another embodiment, the substrate alloy comprises 97.5 wt % Zr and 2.5 wt % Nb. In yet another embodiment, the substrate alloy is made from 35 wt % Zr, 10 wt % Nb and 55 wt % Ti.

Because the improved characteristics of the diffusion hardened zone of the present disclosure allows it to serve as a good bearing material, in some embodiments, the bearing surface consists only of the diffusion hardened zone, where there is no oxide layer on top of the diffusion hardened zone.

In addition to providing improved damage resistance, thereby minimizing debris formation and wear, the diffusion hardened composition of the present disclosure allows for the contact areas between mobile implant components to be maximized, thereby decreasing stress exerted on the components and minimizing the wear damage over time. In the preferred embodiment, the bearing surfaces are maintained at a certain ratio. Specifically, the ratio is maintained at 1:1.05 maximum where the radius of the smaller spherical surface is at 1 and radius of the larger spherical surface is at 1.05. This allows for maximum contact area between the two contact surfaces while allowing relative motion between the two surfaces. The diffusion hardened material of the present disclosure allows for this ratio because of its improved wear resistance, increased hardness and resistance to damage once the oxidized layer has been breached. This ratio is similar to predicate devices with different bearing materials.

Other tri-component implants that can benefit from the improved wear resistant of the diffusion hardened composition of the present disclosure includes ankle, spinal, and bi-polar hip implants. FIGS. 6-10 illustrate various tri-component ankle prostheses of 600, 700, 800, 900, and 1000, respectively. Generally, the implants in FIGS. 6-10 include a platform or talar component 602, 702, 802, 902, and 1002, which is configured to be implanted in the talus, a tibial component 604, 704, 804, 904, and 1004 is configured to be implanted in the distal tibia, and an intermediate bearing component 606, 706, 806, 906, and 1006 is interposed between the talar platform component, e.g., 602, and a tibial component, e.g., 604. The intermediate bearing component may be attached to the tibial component by attachment means known in the art. The articulating distal surface of the insert is configured to articulate against the proximal surface of the talar component.

Typically, the talar platform component and the tibial component are formed with metal such as cobalt chrome, and the intermediate bearing component is made of a softer material such as polyethylene or cross-linked ultra-high molecular weight polyethylene (XLPE). While these materials suffer from the disadvantages discussed above, they are often used instead of ceramics because prior art ceramics are unlikely to withstand the combined stresses typically experienced by these ankle implants.

Referring to FIG. 11, at least the articulating or load bearing surfaces of all three components of the ankle implant comprise the diffusion hardened composition of the present disclosure. In particular, these articulating or load bearing surfaces include (1) the proximal surface of the talar platform component that contacts the intermediate bearing component, (2) the distal surface of the intermediate bearing component, (3) the proximal surface of the intermediate bearing component that contacts the talar component, and (4) the distal surface of the tibial component. As shown, the embodiment comprises two pairs of diffusion hardened surfaces, where the surfaces articulate against and/or exert a force upon one another (e.g., micromotion), depending on whether the implant is fixed or mobile. In the preferred embodiment, all bearing surfaces of the embodiment comprise the diffusion hardened composition of the present disclosure. The benefits discussed above with respect to the improved characteristics of diffusion hardened material of the present disclosure are equally applicable herein.

Figure 12:
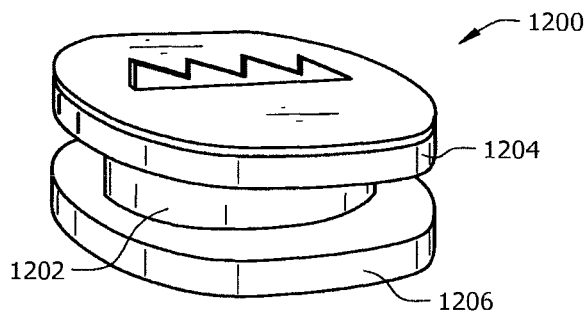
FIGS. 12-14 are perspective views of the various lumbar artificial disc replacements of the present disclosure.
Figure 13:
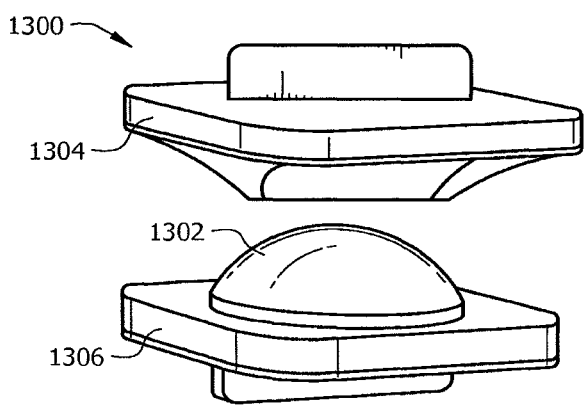
Figure 14:
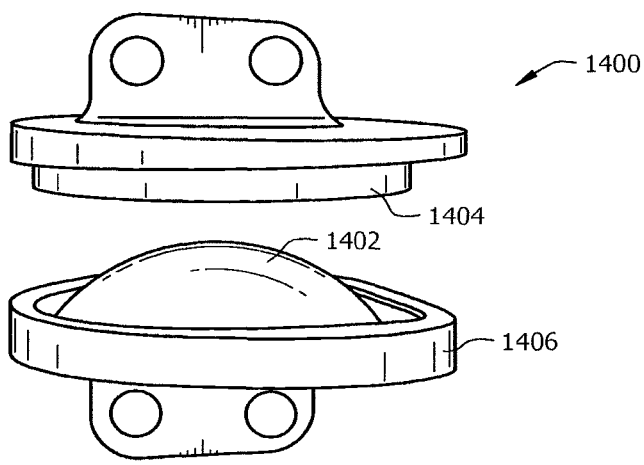

FIGS. 12-14 illustrate exemplary spinal implants, including lumbar artificial disc replacements, labeled as 1200, 1300, and 1400, respectively. Generally, the lumbar artificial disc may have several different designs. For instance, referring to FIG. 12, the lumbar artificial disc 1200 may have a design that resembles a sandwich, where a spacer or insert 1202 is positioned between two endplates: upper endplate 1204 and lower endplate 1206. The insert 1202 fits in between the two metal endplates 1204 and 1206 and is shaped so that the endplates 1204 and 1206 pivot in a way that imitates normal motion of the two vertebrae. The insert 1202 may be mobile or fixed to one of the endplates 1204 and 1206. Referring to FIG. 12, there are small prongs or teeth on one side of each of endplates 3904 and 3906 that help anchor the endplate to the surface of the vertebral body.

Similar to other implants, the upper and lower plates are typically formed from metal such as cobalt chrome, and the intermediate bearing component is made of a softer material such as polyethylene or cross-linked ultra-high molecular weight polyethylene (XLPE). While these materials suffer from the disadvantages discussed above, they are often used instead of ceramics because prior art ceramics are unlikely to withstand the combined stresses typically experienced by these spinal implants.

FIGS. 13 and 14 illustrate another design for a lumbar artificial disc, which is a ball and socket articulation design to allow for normal translation of motion at that segment. Instead of an insert sandwiched between two endplates, the implants 1300 and 1400 of FIGS. 13 and 14 have intermediate component 1302 and 1402, respectively, attached to lower plates 1406, 1406, respectively. The surface of upper plates 1304 and 1404 is concave (not shown) while the surface of intermediate component 1302, 1402 is convex. The concave surfaces of upper plates 1304 and 1404 are designed to fit and articulate against and the convex surfaces of intermediate component 1302 and 1402 to allow for translation of the movement of the vertebrae attached to the plates. Similar to knee and ankle implants, the lumbar artificial disc replacements include constrained and unconstrained designs. The constrained devices provide a fixed center of rotation that does not change. The unconstrained design allows the center of the implant, or insert, to move forward and back slightly during lumbar motion.

In the preferred embodiment, at least the articulating or load bearing surfaces of all three components of the lumbar implant comprise the diffusion hardened composition of the present disclosure, thereby providing the benefits discussed above. In particular, these articulating or load bearing surfaces include (1) the proximal surface of the lower plate that contacts the insert or intermediate bearing component, (2) the distal surface of the insert or intermediate bearing component, (3) the proximal surface of the insert or intermediate bearing component that contacts the upper plate, and (4) the distal surface of the upper plate. As shown, the embodiment comprises two pairs of diffusion hardened surfaces, where the surfaces articulate against and/or exert a force upon one another (e.g., micromotion), depending on whether the implant is fixed or mobile. All of which are the diffusion hardened composition of the present disclosure. The benefits discussed above with respect to the improved characteristics of diffusion hardened material of the present disclosure are equally applicable herein.

Figure 15A:
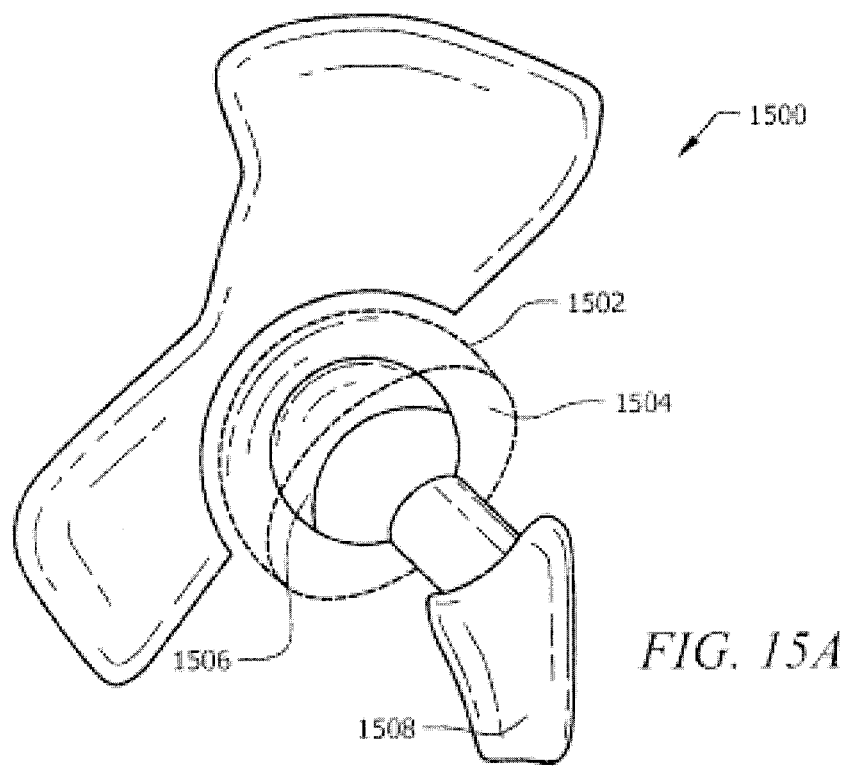
FIGS. 15A and 15B illustrate one embodiment arrangement of a bi-polar hip implant in accordance with the present disclosure.
Figure 15B:
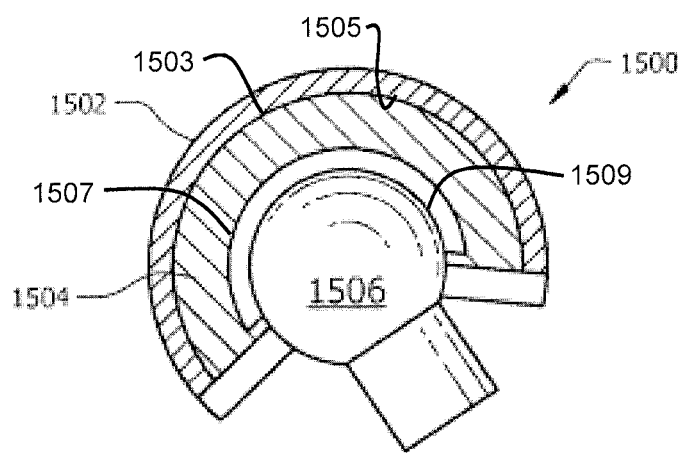

FIGS. 15A and 15B illustrate an exemplary bi-polar hip implant 1500. Generally, the bi-polar hip implant 1500 may include shell 1502, liner 1504, head 1506, and stem 1508. Shell 1502 articulates directly with the hip socket of a patient. Generally, liner 1504 is attached to shell 1502, and head 1506 articulates against and rotates within liner 1504. Typically, as in other implants, the shell 1502 and head 1506 are formed with metals while the liner 1504 comprises a softer material such as polyethylene. As such, conventional bi-polar hip implants suffer from the disadvantages discussed above.

In the preferred embodiment, the bearing or articulating surfaces of all three components: shell 1502, liner 1504, and head 1506 comprise the diffusion hardened composition of the present disclosure. In other words, the diffusion hardened surfaces include interior surface 1503 of shell 1502, the outer surface 1505 of liner 1502 bearing against such interior surface 1503, the interior surface 1507 of liner 1504, the articulating surface 1509 of head 1506. The benefits discussed above with respect to the improved characteristics of diffusion hardened material of the present disclosure are equally applicable herein.

Figure 16:
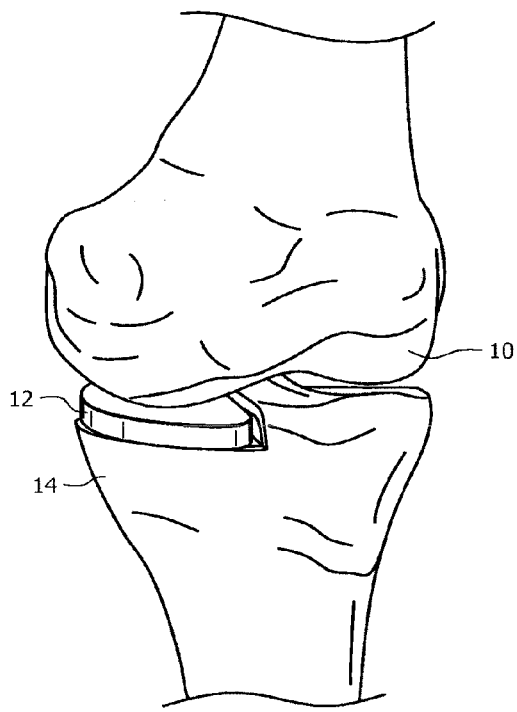
FIG. 16 is a prospective view of an embodiment of the present disclosure in operative association with a tibia and a femur.
Figure 17:
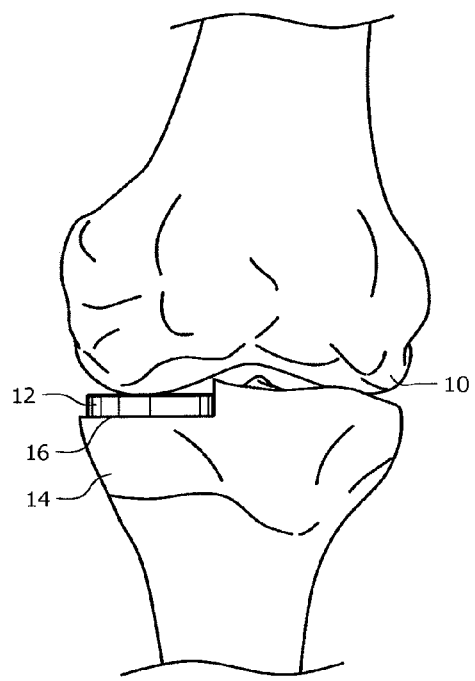
FIG. 17 is a side view of the embodiment of the present disclosure shown in FIG. 1.

In another aspect of the present disclosure, the diffusion hardened load bearing surface of the present disclosure provides highly compatible and superior bearing surface having improved properties, such as low-friction wear couple, with natural articulating cartilage. In FIGS. 16 and 17, a typical hemiarthroplasty implant that is fixed to a patient's tibia is shown. In the preferred embodiment, the articulating or bearing surfaces of the tibial hemi-arthroplasty component 12 that contact the natural cartilage of a femur 10 comprise a diffusion hardened composition of the present disclosure. The diffusion hardened composition of the present disclosure improves the articulation between component 12 with natural cartilage of the femur 10 because the diffusion hardened surface of the present disclosure has the low wear, low friction material properties of a ceramic while providing improved wear resistant and hardness over prior art ceramics. Referring to FIGS. 16 and 17, the tibial hemi-arthroplasty component 12 is attached to the proximal portion of a prepared tibia 14. The tibial hemi-arthroplasty component 12 provides a preferably distal surface that communicates the prepared surface of the tibia 14. Also, tibial hemi-arthroplasty component 12 preferably provides a proximal articulating/bearing surface that is either substantially leveled (or even) or contoured, where the surface articulates against the natural articulating cartilage of femur 10.

In certain embodiments with the contoured articulating/bearing surface, the distal surface of component 12 comprises a concave or convex profile with a preferred spherical radius of curvature no less than 3 inches. In the preferred embodiment, at least one articulating surface of the tibial hemi-arthroplasty component 12 comprises a diffusion hardened composition of the present disclosure. In other embodiments, the entire surface of the tibial hemi-arthroplasty component 12 may comprise the diffusion hardened composition of the present disclosure, or, only certain bearing surface portions of the implant may comprise an outer layer of diffusion hardened composition of the present disclosure. The diffusion hardened substrate of the present disclosure may be zirconium, titanium, hafnium, and niobium or their respective alloys, and may include nitride materials that have been produced according to the aspects of the present disclosure.

Referring to FIGS. 16-18, in this embodiment, which may be referred to as an "onlay" embodiment, a significant portion the proximal end of the tibia 14 has been resected to provide a prepared recess area 16 to receive the tibial hemi-arthroplasty component 12. The onlay embodiment may include a total resection of one side of the tibia, e.g., a full anterior to posterior resection of the tibial side, thereby sacrificing the meniscus. In these cases, it is desirable to have the tibial hemi-arthroplasty component 12 cover a majority of the resected tibial plateau surface area 16.

A meniscus-sparing "inlay" embodiment may also be employed. The inlay embodiment requires minimal or no resection of the tibia. For example, referring to FIG. 19, a slight resection 18 of the tibia 14 may be prepared to receive a desired tibial hemi-arthroplasty component, such as one shown in FIGS. 20A-20J. The prepared recess 18 may be any shape or size necessary to accommodate the desired tibial hemi-arthroplasty component. As shown in FIG. 19, the periphery and menisci of the tibia 14 may be preserved by the inlay embodiment because it does not involve the total resection shown in FIGS. 16-18. As mentioned, the inlay embodiment may not require a prepared recess or other feature such as a drilled hole in order to be fixed to the tibia. Instead, inlay may only require a minimally-invasive impact force to secure it to the proximal tibia.

The procedure is minimally invasive because it requires an incision that is just large enough to fit the inlay component through the incision. For insertion, the knee is flexed to an angle sufficient to expose the proximal tibia through the incision. The inlay component, held by an external tool, is inserted through the incision and aligned on the proximal tibia. Once positioned, an impact force on the tool seats the inlay component on the tibia for fixation. The fixation means of the inlay component could be either bone cement or an ingrowth surface on the component, as discussed further below.

Referring to FIGS. 20A-20J, the tibial hemi-arthroplasty component 12 of both the onlay and inlay embodiments of the present disclosure may be in the form of a button or dart having an enlarged head 54 that has an articulating surface portion 56. In the preferred embodiment, the articulating surface 56 comprises a diffusion hardened surface prepared according to the present disclosure. Referring to FIGS. 18-20, the tibial hemi-arthroplasty component 12 may be placed within a central prepared tibial recess 16 or 18. Referring to FIG. 20, the tibial hemi-arthroplasty component 52 may have a radius on the entire proximal, outside edge or chambered peripheral edges on the head 54 to avoid impingement with articulating cartilage and/or soft tissue (e.g., the anterior and posterior cruciate ligaments).

Referring to FIGS. 16-20, the tibial hemi-arthroplasty component 12 may have any available or conventional means for attachment to the proximal tibia 14. Attachment means may be any suitable means including, but not limited to, screws/pins, spikes, barbed shafts, geometries adapted for interference fit, splines, multiple prongs, pegs, waffle forms, sharp hook features, blades, fins, fluted shafts, circumferential rings, porous coatings/scaffolds, cement fixation, or a combination thereof. Also, attachment means may be any suitable means known to those skilled in the art.

Referring to FIG. 20, the attachment means of tibial hemi-arthroplasty component 12 may include one or more keels 58 extending in the anterior-posterior direction, as shown in FIGS. 20A-20D and 20E-20I. The tibial hemi-arthroplasty component 12 may also have one or more keels 60 extending in the medial-lateral direction for tibial fixation and stability as shown in FIGS. 20E and 20J. However, the keels 58 and 60 may also extend in other directions. Attachment means, particularly keels 58 and 60, may vary in geometry to suit a particular patient. Tibial hemi-arthroplasty component 12 may be a customized implant designed to suit a particular individual's needs. The diffusion hardened composition of the present disclosure, when used in tibial hemi-arthroplasty or other implant applications that requires articulation of the natural articulating cartilage and an implant surface, reduces the rate of small wear particle, overall wear, and cartilage wear between an implant's surface and natural articulating cartilage.

Referring to FIGS. 20A-20E, the tibial hemi-arthroplasty component 12 of the present disclosure may be a one-piece homogeneous device. In FIG. 21, the components of a knee with only the tibial hemi-arthroplasty component 12 implanted is schematically demonstrated. Specifically, FIG. 21 is a representation of the arrangement of one embodiment showing the tibial component attached to the tibia and having a surface that contacts the articular cartilage of the femur. The contacting surface comprises a diffusion hardened composition of the present disclosure (referred to as "ODH" in FIG. 21). Alternatively, referring to FIGS. 20E-20J, the tibial hemi-arthroplasty component 12 may be a multiple-piece apparatus, such as in combination with an insert 22, which can be fixed or mobile.

In another aspect of the disclosure, the tibial hemi-arthroplasty component 12 may have porous structures or coatings on the attachment means, e.g., keels 58 and/or 60, for attachment to the proximal tibia to improve osseointegration. Moreover, attachment means, e.g., keels 58 and/or 60 may comprise a bioactive material such as hydroxyapatite, Bone Morphogenic Proteins (BMPs), fluoride, and/or calcium, etc. to encourage bone ingrowth.

In other embodiments, the tibial hemi-arthroplasty component 12 is also advantageously adapted for reduced backside wear with either fixed or mobile-bearing tibial inserts. While the Figures and discussion thus far relate to a tibial hemi-arthroplasty component, it is not meant to limit the scope of the invention, and reference to tibial hemi-arthroplasty component may refer to the tibial component or tray in a total knee replacement or total knee arthroplasty. In total knee replacements, the tibial component replaces the patient's entire proximal tibial surface, while a unicompartmental tibial replacement replaces just part of the tibial surface. In a total knee replacement it is necessary to replace the entire tibial surface due to the patient having disease present in more than one compartment.

Referring to FIGS. 20E-20J, in fixed bearing replacements, the distal surface of insert 22 is preferably substantially leveled or even to communicate with a substantially leveled or even proximal surface of component 12. The insert 22 is affixed to component 12 by any suitable means available and known to those skilled in the art, including but not limited to screws, locking mechanisms, adhesives, interlocking channels, and bone cement. The proximal surface of insert 22 may be concave or convex, depending on the desired applications. For instance, in hemi-arthroplasty, unicompartmental replacement, or bi-compartmental replacements, a relatively substantially leveled or even surface is desirable. On the other hand, for a total knee replacement, a concave or convex or combination is preferred to conform to the femoral component for additional stability as the anterior cruciate ligament is removed in a total knee replacement. The improved wear resistant and hardness characteristics of the diffusion hardened material of the present disclosure, when used in combination with polyethylene and XLPE, also minimize the amount of backside wear or release of implant particles due to the micromotion between the non-articulating surfaces. In the preferred embodiment, both the distal surface of insert 12 that is affixed to component 12 and the proximal surface of insert 12 that contacts the articular cartilage comprise the diffusion hardened composition of the present disclosure.

In some embodiments, the diffusion hardened zone of the present disclosure acts as the bearing surface and articulates against the natural articulating cartilages, such as described with respect to FIGS. 16-20 above. In other embodiments, the diffusion hardened zone of the present disclosure acts as a bearing surface and articulates against an oxidized material an oxide layer, where the oxidized material may be produced according to the present disclosure or other known methods. In yet other embodiments, the diffusion hardened zone of the present disclosure articulates against another diffusion hardened zone, where the other diffusion hardened zone may be produced by other known methods.

While the disclosures of U.S. Pat. No. 7,550,209 to Pawar et al. and co-pending U.S. application Ser. Nos. 12/127,413 and 12/244,492 describing the diffusion hardened composition of the present disclosure and method of making same have been incorporated by reference, certain exemplary features of the diffusion hardened composition of the present disclosure are discussed in the paragraphs above and are also set forth below. The diffusion hardened zone of the compositions of the present disclosure has a layered structure, such as the diffusion hardened zone shown in FIGS. 5B-5C. The thickness of the diffusion hardened zone of the present disclosure is at least equal to that of the ceramic (oxide) layer formed on the surface of such an implant, e.g., shown in FIGS. 5B-5C.

The oxygen concentration at the interface (between the oxide and diffusion hardened zone) is approximately equal to the solubility limit of oxygen in alpha zirconium which is approximately 9% (w/w) or 30 atomic %. The diffusion hardened composition of the present disclosure has an oxygen concentration profile of greater than 15 microns. The depth of hardening in the micro-hardness profiles of the diffusion hardened composition of the present disclosure can follow an exponential, error function type of profile or a combination of uniform and error/exponential function. Further, higher micro-hardness of the diffusion hardened composition of the present disclosure e.g., about 500 to about 1000 Knoop 10 g, can extend further into the substrate, e.g., about 5 to 55 microns from the interface between the oxide and diffusion hardened zone.

In another embodiment, the diffusion hardened composition of the present disclosure has a diffusion hardened zone that is characterized by at least three layers. The first layer is beneath the oxide layer, the second layer is beneath the first layer and the third layer is beneath the second layer. The thickness of the first layer is greater than the second layer and thickness of second layer may be greater than the third layer. In another embodiment, the layers of the diffusion hardened zone may have similar thicknesses. In one aspect of this disclosure, the oxide layer is preferentially retained on the surface of the substrate. In one embodiment, the monoclinic content of the diffusion hardened composition of the present disclosure is typically greater than 96% (v/v), and preferably between about 97 and 98%.

For embodiments with substrates comprising Zr—Nb-based alloys, the diffusion hardened zone can be 70 micron or greater. As stated previously, the diffusion hardened zone may comprise more than one layer and is underneath the ceramic layer. In one embodiment, the Zr-2.5 Nb comprises two phases, alpha (hexagonal) and beta (cubic). The diffusion hardened zone is predominantly alpha phase (hexagonal). A minor amount of beta (cubic) phase (less than 7% (v/v)) can be present in the first layer of diffusion hardened zone. The first layer is predominantly alpha phase and the volume fraction of beta phase gradually increases in the diffusion layer towards the substrate. If the zirconium alloy is predominantly single phase (alpha) then the beta phase in the diffusion hardened zone will be significantly less than it is in the substrate.

In embodiments with an oxide layer, the oxide layer of the diffusion hardened composition of the present disclosure is substantially defect-free. Typically, the defects in the oxide layer can be broadly classified as pores and cracks. The pores can be circular or elongated and may be on the surface or at the interface. The cracks can be perpendicular to the oxide metal interface, and/or may be parallel to the oxide metal interface. Another type of defect that is anticipated in this disclosure is the wavy oxide metal interface and delaminated or spalled oxide. The defects in the ceramic layer may be evaluated on a cross-sectional metallographic sample at 1000× magnification with field of view of approximately 100×80 microns.

In another embodiment, the ceramic layer of the diffusion hardened composition of the present disclosure comprises a distinct secondary phase through the entire thickness of the ceramic layer. In one embodiment of the composition of the present disclosure, when the ceramic layer is retained on the surface, the composition comprises a metallic hardened surface formed on top of the ceramic layer along with the diffusion hardened zone formed underneath the ceramic layer. This layer may or may not be retained on the final medical implant.

The diffusion hardened composition of present disclosure can be produced by employing three processes. All processes can be performed in a single or multiple steps. The processes are (1) ceramic layer formation (i.e., oxidation, nitridation, boridation, carburization, or any combination thereof), (2) diffusion hardening, and optionally, (3) ceramic layer formation. If ceramic layer is retained on the surface during the diffusion hardening, process 1 and 2 may be sufficient. If the final application is such that a ceramic layer is not required on the surface, temperature and time are chosen in such a way that process 2 will dissolve the ceramic layer completely. Alternatively, the surface ceramic layer may be removed by mechanical, chemical or electrochemical means. As mentioned, when the ceramic layer is retained on the surface during process 2, there can be formation of a metallic hardened layer on the oxide layer. This metallic hardened layer may or may not be removed for the final product. If the ceramic layer is completely dissolved into the substrate and re-formation of the ceramic layer is desired then a diffusion profile is obtained which will produce a high integrity and defect-free ceramic layer during the ceramic layer formation process. This diffusion profile can be an exponential function, an error function, a uniform, or any sequential combination thereof. It should be noted that some of these functions may also be attributed to be linear or higher order polynomials. It should be noted that the combination of diffusion profile and retained oxide is obtained through careful control of time, temperature and pressure during ceramic layer formation process and diffusion hardening process. It should be understood that variations by way of substitutions and alterations from these general processes described above which do not depart from the spirit and scope of the invention are understood to be within the scope of the invention. In this way, the general processes described are merely illustrative and not exhaustive.

Although the embodiments of the present disclosure and their advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A medical implant, comprising:
   a shell having an interior surface;
   a liner having an inner surface and an outer surface, the outer surface positioned in contact with the interior surface of the shell;
   a head coupled to a stem, the head having an exterior surface positioned in contact with the inner surface of the liner;
   wherein at least a portion of each of the interior surface of the shell, the inner and outer surfaces of the liner, and the exterior surface of the head comprises:
     a diffusion hardened zone; and
     a substantially defect-free ceramic layer overlaying the diffusion hardened zone; and
   wherein the ceramic layer has a thickness of about 0.1 to 25 microns and the diffusion hardened zone has a thickness of greater than 2 microns.

2. The medical implant of claim 1, wherein the liner is attached to the shell.

3. The medical implant of claim 1, wherein at least one of the interior surface of the shell, the inner and outer surfaces of the liner, and the exterior surface of the head further comprises a metallic hardened layer in contact with the top of the ceramic layer.

4. The medical implant of claim 1, wherein the ceramic layer comprises a secondary phase, the secondary phase being distinct through a thickness of the ceramic layer; and
   wherein the diffusion hardened zone has a layered structure comprising at least two distinct layers under metallographic analysis.

5. The medical implant of claim 1, wherein the exterior surface of the head comprises an articulating surface positioned to articulate against the inner surface of the liner.

6. The medical implant of claim 1, wherein the outer surface of the liner is positioned to articulate against the interior surface of the shell.

7. A medical implant, comprising:
   a shell, a liner, a head portion, and a stem portion extending from the head portion, at least one of the liner and the head portion having a first bearing surface defining a first radius, and at least one of the shell and the liner including a second portion having a second bearing surface defining a second radius;
   wherein the first bearing surface is configured to contact the second bearing surface, and wherein a maximum ratio between the first radius and the second radius is 1:1.05; and
   wherein a portion of each of the shell, the liner, and the head portion, include the first and second bearing surfaces, and comprise:
     a diffusion hardened zone in contact with a substrate;
     a substantially defect-free ceramic layer overlaying the diffusion hardened zone, wherein the ceramic layer has a thickness of about 0.1 to 25 microns and the diffusion hardened zone has a thickness of greater than 2 microns.

8. The medical implant of claim 7, wherein the first bearing surface comprises an outer surface of the liner and the second bearing surface comprises an interior bearing surface of the shell, and wherein the liner is coupled to the shell.

9. The medical implant of claim 7, wherein at least one of the first and second bearing surfaces further comprises a metallic hardened layer in contact with the ceramic layer.

10. The medical implant of claim 7, wherein the ceramic layer comprises a secondary phase, the secondary phase being distinct through the entire thickness of the ceramic layer.

11. The medical implant of claim 10, wherein the diffusion hardened zone has a layered structure comprising at least two distinct layers under metallographic analysis.

12. The medical implant of claim 7, wherein at least a portion of the first and second bearing surfaces comprises the diffusion hardened zone.

13. A medical implant, comprising:
    a shell component having a first surface;
    a head component coupled to a stem component, the head component having a second surface; and
    an insert configured to be interposed between the shell component and the head component, the insert having a third surface and a fourth surface;
    wherein the first surface is configured to be in generally opposing facing relation with the third surface, and wherein the first surface is configured to articulate against the third surface;
    wherein the second surface is configured to be in generally opposing facing relation with the fourth surface;
    wherein a portion of each of the first, second, third, and fourth surfaces comprises:
      a diffusion hardened zone in contact with a substrate;
      a substantially defect-free ceramic layer overlaying the diffusion hardened zone, wherein the ceramic layer has a thickness of about 0.1 to 25 microns and the diffusion hardened zone has a thickness of greater than 2 microns.

14. The medical implant of claim 13, wherein the second surface is attached to the fourth surface.

15. The medical implant of claim 13, wherein the diffusion hardened zone has a thickness of greater than 5 microns.

16. The medical implant of claim 13, wherein the ceramic layer comprises a secondary phase, the secondary phase being distinct through a thickness of the ceramic layer.

17. The medical implant of claim 16, wherein the diffusion hardened zone has a layered structure comprising at least two distinct layers under metallographic analysis.

18. The medical implant of claim 13, wherein the first surface has a first radius, wherein the third surface has a second radius, and wherein a maximum ratio between the second radius and the first radius is 1:1.05.

19. The medical implant of claim 13, wherein the fourth surface has a first radius, wherein the second surface has a second radius, and wherein a maximum ratio between the second radius and the first radius is 1:1.05.

* * * * *